United States Patent
Chinta et al.

(10) Patent No.: US 9,764,996 B2
(45) Date of Patent: Sep. 19, 2017

(54) CATALYSTS CONTAINING NANO-MATERIALS AND METHODS OF MAKING AND USING SAME

(71) Applicant: FINA TECHNOLOGY, INC., Houston, TX (US)

(72) Inventors: Sivadinarayana Chinta, Sugar Land, TX (US); Joseph L. Thorman, Helsinki (FI)

(73) Assignee: FINA TECHNOLOGY, INC., Houston, TX (US)

(*) Notice: Subject to any disclaimer, the term of this patent is extended or adjusted under 35 U.S.C. 154(b) by 525 days.

(21) Appl. No.: 14/294,905

(22) Filed: Jun. 3, 2014

(65) Prior Publication Data
US 2014/0288341 A1    Sep. 25, 2014

Related U.S. Application Data

(62) Division of application No. 12/938,453, filed on Nov. 3, 2010, now Pat. No. 8,791,040.

(51) Int. Cl.
| | | |
|---|---|---|
| *C07C 2/66* | (2006.01) | |
| *C07C 2/86* | (2006.01) | |
| *B01J 29/068* | (2006.01) | |
| *B01J 29/072* | (2006.01) | |
| *B01J 29/08* | (2006.01) | |
| *B01J 35/00* | (2006.01) | |
| *B01J 37/02* | (2006.01) | |
| *B82Y 30/00* | (2011.01) | |

(52) U.S. Cl.
CPC ............ *C07C 2/867* (2013.01); *B01J 29/068* (2013.01); *B01J 29/072* (2013.01); *B01J 29/084* (2013.01); *B01J 35/002* (2013.01); *B01J 35/006* (2013.01); *B01J 37/0246* (2013.01); *B82Y 30/00* (2013.01); *C07C 2/864* (2013.01); *C07C 2/865* (2013.01); *C07C 2529/06* (2013.01); *C07C 2529/72* (2013.01); *C07C 2529/78* (2013.01)

(58) Field of Classification Search
CPC .................................... C07C 2/66; C07C 2/86
USPC ................................ 585/469, 436, 437, 438
See application file for complete search history.

(56) References Cited

U.S. PATENT DOCUMENTS 4,499,317 A * 2/1985 Liu ........................ B01J 29/14
585/437

* cited by examiner

*Primary Examiner* — Thuan D Dang
(74) *Attorney, Agent, or Firm* — Albert Shung

(57) ABSTRACT

A method of making a catalyst containing nanosize zeolite particles supported on a support material is disclosed. A process for making styrene or ethylbenzene by reacting toluene with a $C_1$ source over a catalyst containing nanosize zeolite particles supported on a support material is disclosed.

9 Claims, 5 Drawing Sheets

CATALYSTS CONTAINING NANO-MATERIALS AND METHODS OF MAKING AND USING SAME

CROSS-REFERENCE TO RELATED APPLICATIONS

This application is a Divisional of U.S. application Ser. No. 12/938,453, filed on Nov. 3, 2010.

FIELD

The present invention is generally related to the production of styrene and ethylbenzene. More, specifically, the embodiments of the present invention relate to catalysts for the production of styrene and ethylbenzene.

BACKGROUND

Styrene is an important monomer used in the manufacture of many polymers. Styrene is commonly produced by forming ethylbenzene, which is then dehydrogenated to produce styrene. Ethylbenzene is typically formed by one or more aromatic conversion processes involving the alkylation of benzene.

Aromatic conversion processes, which are generally carried out utilizing a molecular sieve type catalyst, are well known in the chemical processing industry. Such aromatic conversion processes include the alkylation of aromatic compounds such as benzene with ethylene to produce alkyl aromatics, such as ethylbenzene. Other alkylation processes include the alkylation of toluene with methanol and/or formaldehyde to produce styrene and ethylbenzene. Unfortunately, these alkylation processes have generally been characterized by low yields of desired products and low selectivity to styrene and ethylbenzene.

The molecular sieve catalysts that are suitable for use in these alkylation reactions typically include zeolites. The most commercially available zeolites are prepared such that the zeolite crystal is greater than 1 µm.

In view of the above, it would be desirable to develop processes of forming styrene and/or ethylbenzene capable of increased yields and improved selectivity.

SUMMARY

Embodiments of the present invention include a method of making an alkylation catalyst by providing a nanosize zeolite and contacting it with a solution to create a dispersion solution having dispersed nanosize zeolite particles. The dispersion solution is contacted with a support material to create a wetted support. The wetted support is dried to obtain a catalyst that includes a nanosize zeolite.

The nanosize zeolite can have a particle size of less than 1000 nm or less than 300 nm and can be formed from a faujasite, such as an X-type or Y-type zeolite. The support material can be selected from the group consisting of silica, alumina, aluminosilica, titania, and zirconia and combinations thereof. The catalyst can include a promoter selected from the group consisting of Ru, Rh, Ni, Co, Pd, Pt, Mn, Ti, Zr, V, Nb, K, Cs, Ga, P, B, Rb, Ag, Ge, Cu, Mg, and Na and combinations thereof.

An alternate embodiment of the present invention is a method of making a catalyst for styrene production by contacting a nanosize zeolite with a solution to create a dispersion solution having dispersed nanosize zeolite particles. A nanocarrier is added to the dispersion solution that is contacted with a support material to create a wetted support. The wetted support is then dried to obtain a catalyst comprising a nanosize zeolite. The nanocarrier can be any material having an electrostatic interaction with the zeolite material, or that includes material that can attract nanoparticles with columbic interaction, such as for example a silica oxide material or a boehmite alumina material.

A further embodiment of the present invention is a styrene production process that includes contacting a carbon ($C_1$) source with toluene in the presence of a catalyst disposed within a reactor to form a product stream comprising styrene. The catalyst includes a nanosize zeolite.

DETAILED DESCRIPTION

Figure 1:
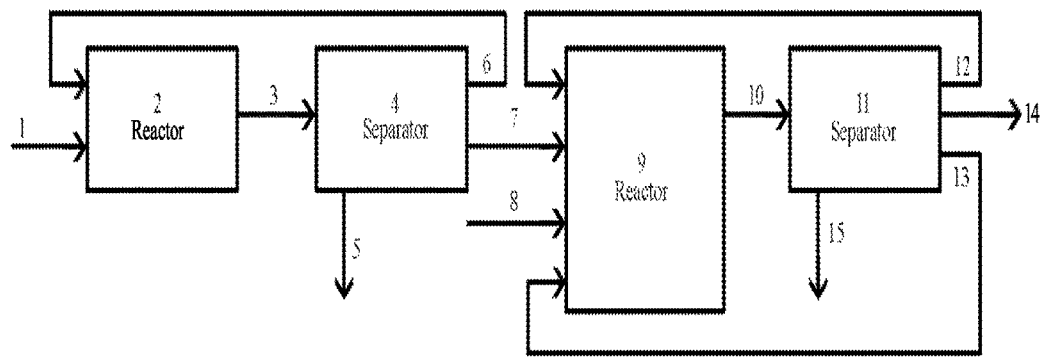
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Styrene production processes generally include reacting toluene with methanol or methane/oxygen as co-feed. In practice, the methanol ($CH_3OH$) often dehydrogenates into side-products, resulting in lower than desired toluene conversion and/or lower than desired selectivity. As used herein, the term "selectivity" refers to the percentage of input/reactant converted to a desired output/product. Such low conversion/selectivity rates generally lead to processes that are not economical.

However, the processes described herein (and particularly the catalysts described herein in combination with the described processes) are capable of minimizing side product formation, thereby resulting in increased conversion and/or selectivity.

In one or more embodiments, the styrene production processes include reacting toluene with a carbon source, which can be referred to as a $C_1$ source (e.g., a carbon source capable of cross-coupling with toluene to form styrene, ethylbenzene or combinations thereof), in the presence of a catalyst to produce a product stream including styrene and ethylbenzene. For example, the $C_1$ source may include methanol, formaldehyde or a mixture thereof. Alternatively, the $C_1$ source includes toluene reacted with a $C_1$ source selected from one or more of the following: formalin (37 wt. % to 50 wt. % $H_2CO$ in a solution of water and MeOH), trioxane (1,3,5-trioxane), methylformcel (55 wt. % $H_2CO$ in methanol), paraformaldehyde and methylal (dimethoxymethane). In another embodiment, the $C_1$ source is selected from methanol, formaldehyde, formalin, trioxane, methylformcel, paraformaldehyde, methylal, dimethylether, dimethoxyethane, and combinations thereof.

Formaldehyde can be produced by the oxidation or dehydrogenation of methanol, for example. In one embodiment, formaldehyde is produced by the dehydrogenation of methanol to produce formaldehyde and hydrogen gas. This reaction step generally produces a dry formaldehyde stream, thereby eliminating separation of formed water prior to the reaction of the formaldehyde with toluene. The dehydrogenation process is described in the equation below:

$$CH_3OH \rightarrow CH_2O + H_2$$

Formaldehyde can also be produced by the oxidation of methanol to produce formaldehyde and water. The oxidation of methanol is described in the equation below:

$$2CH_3OH + O_2 \rightarrow 2CH_2O + 2H_2O.$$

When utilizing a separate process to obtain formaldehyde, a separation unit may then be used to separate the formaldehyde from the hydrogen gas or water from the formaldehyde and unreacted methanol prior to reacting the formaldehyde with toluene for the production of styrene. Such separation inhibits hydrogenation of the formaldehyde back to methanol. The formaldehyde can then be sent to a styrene reactor and the unreacted methanol recycled, for example.

Although the equations illustrated above show a 1:1 molar ratio of toluene and the $C_1$ source, such molar ratio is not limited within the embodiments herein and can vary depending on operating conditions and efficiency of the reaction system. For example, if excess toluene or $C_1$ source is fed to the reaction zone, the unreacted portion can be subsequently separated and recycled back into the process. In one embodiment the molar ratio of toluene:$C_1$ source can range from 100:1 to 1:100. In alternate embodiments, the molar ratio of toluene:$C_1$ source can range from 50:1 to 1:50, or from 20:1 to 1:20, or from 10:1 to 1:10, or from 5:1 to 1:5 or from 2:1 to 1:2, for example.

The styrene production process generally includes catalyst disposed within one or more reactors. The reactors may include fixed bed reactors, fluid bed reactors, entrained bed reactors or combinations thereof, for example. Reactors capable of operation at the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention.

In another aspect, the one or more reactors may include one or more catalyst beds. When utilizing multiple beds, an inert material layer may separate each bed. The inert material may include any type of inert substance, such as quartz, for example. In one or more embodiments, the reactor includes from 1 to 10 catalyst beds, or from 2 to 8 catalyst beds, or from 2 to 6 catalyst beds, for example. The $C_1$ source and toluene may be injected into a catalyst bed, an inert material layer or combinations thereof, for example. Both the $C_1$ source and toluene may be injected into a catalyst bed, optionally both the $C_1$ source and toluene may be injected into an inert material layer. Alternatively, at least a portion of the $C_1$ source may be injected into a catalyst bed(s) and at least a portion of the toluene feed is injected into an inert material layer(s). In yet another embodiment, the entire $C_1$ source may be injected into a catalyst bed(s) and all of the toluene feed is injected into an inert material layer(s). Alternatively, at least a portion of the toluene feed may be injected into a catalyst bed(s) and at least a portion the $C_1$ source may be injected into an inert material layer(s). In yet another embodiment, all of the toluene feed may be injected into a catalyst bed(s) and the entire $C_1$ source may be injected into an inert material layer(s).

The operating conditions of the reactors will be system specific and can vary depending on the feedstream composition and the composition of the product streams. In one or more embodiments, the reactor(s) may operate at elevated temperatures and pressures, for example.

In one or more embodiments, the elevated temperature can range from 250° C. to 750° C., or from 300° C. to 500° C. or from 325° C. to 450° C., for example. The pressure can range from 0.1 atm to 70 atm, or from 0.1 atm to 35 atm, or from 1 atm to 5 atm, for example.

FIG. 1 illustrates a simplified flow chart of one embodiment of the styrene production process described above wherein the $C_1$ source is formaldehyde. In this embodiment, a first reactor (2) is either a dehydrogenation reactor or an oxidation reactor. First reactor (2) is designed to convert a first methanol feed (1) into formaldehyde. The product stream (3) of the first reactor (2) may then be sent to an optional gas separation unit (4) where the formaldehyde is separated from any unreacted methanol (6) and unwanted byproducts (5). Any unreacted methanol (6) can then be recycled back into the first reactor (2). The byproducts (5) are separated from the clean formaldehyde (7).

In one embodiment, the first reactor (2) is a dehydrogenation reactor that produces formaldehyde and hydrogen and the gas separation unit (4) is a membrane capable of removing hydrogen from the product stream (3).

In an alternate embodiment, the first reactor (2) is an oxidative reactor that produces product stream (3) comprising formaldehyde and water. The product stream (3) comprising formaldehyde and water can then be sent to the second reactor (9) without a gas separation unit (4).

The clean formaldehyde (7) is then reacted with a feed stream of toluene (8) in the second reactor (9) in the presence of a catalyst (not shown) disposed in the second reactor (9). The toluene and formaldehyde react to produce styrene. The product (10) of the second reactor (9) may then be sent to an optional separation unit (11) where any unwanted byproducts (15), such as water, can be separated from the styrene, unreacted formaldehyde (12) and unreacted toluene (13). Any unreacted formaldehyde (12) and unreacted toluene (13) can be recycled back into the second reactor (9). A styrene product stream (14) can be removed from the separation unit (11) and subjected to further treatment or processing if desired.

Figure 2:
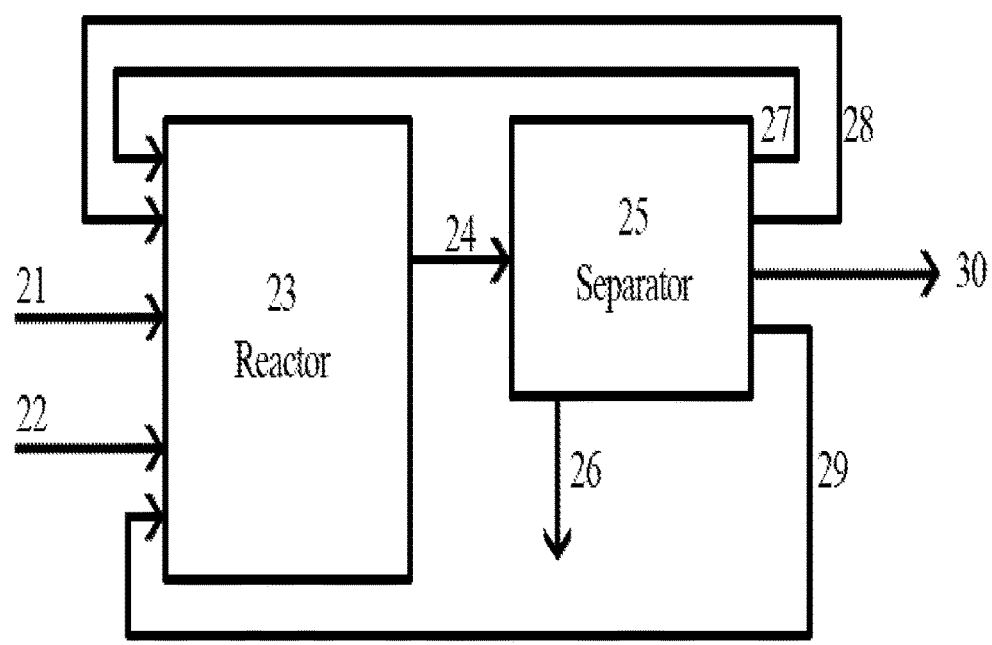
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 2 illustrates a simplified flow chart of another embodiment of the styrene process discussed above wherein the $C_1$ source is methanol. A methanol containing feed stream (21) is fed along with a feed stream of toluene (22) to a reactor (23) having a catalyst (not shown) disposed therein. The methanol reacts with the catalyst to produce a product (24) including styrene. The product (24) of the reactor (23) may then be sent to an optional separation unit (25) where any unwanted byproducts (26) can be separated from the styrene, unreacted methanol (27), unreacted formaldehyde (28) and unreacted toluene (29). Any unreacted methanol (27), unreacted formaldehyde (28) and unreacted toluene (29) can be recycled back into the reactor (23). A styrene product stream (30) can be removed from the separation unit (25) and subjected to further treatment or processing if desired.

The catalyst utilized for the processes described herein generally includes a zeolitic material. As used herein, the term "zeolitic material" refers to a molecular sieve containing an alumino silicate lattice. Zeolitic materials are well known in the art and possess well-arranged pore systems with uniform pore sizes. However, these materials tend to possess either only micropores or only mesopores, in most cases only micropores. Micropores are defined as pores having a diameter of less than about 2 nm. Mesopores are defined as pores having a diameter ranging from about 2 nm to about 50 nm. Micropores generally limit external molecules access to the catalyticly active sites inside of the micropores or slow down diffusion to the catalyticly active sites.

Embodiments of the present invention utilize a nanosize zeolite. As used herein, the term "nanosize zeolite" refers to zeolitic materials having a particle size smaller than 1000 nm (1 µm). For example, the particle size may be less than 1000 nm, or less than 300 nm, or less 100 nm, or less than 50 nm, or less than 25 nm, for example. In one or more embodiments, the particle size is from 1.0 nm to 1000 nm, or from 10 nm to 500 nm, or from 25 nm to 300 nm, or from 50 nm to 100 nm or from 50 nm to 75 nm, for example. As used herein, the "particle size" refers to either the size of each discrete crystal (i.e., crystal) of the zeolitic material or the size of an agglomeration of particles (i.e., crystallite) within the zeolitic material. The particles of nanosize zeolite may also be referred to as nanoparticles.

The zeolitic materials may include silicate-based zeolites, such as faujasites and mordenites, for example. Silicate-based zeolites may be formed of alternating $SiO_2$ and $MO_x$ tetrahedra, where M is an element selected from the Groups 1 through 16 of the Periodic Table. Such formed zeolites may have 4, 6, 8, 10, or 12-membered oxygen ring channels, for example. An example of a faujasite are X-type and Y-type zeolites. The zeolitic material may have a Si/Al ratio of 1.0 or greater. In an embodiment the Si/Al ratio can range from 1.0 to 200. In an alternate embodiment the Si/Al ratio can range from 1.0 to 100. In an alternate embodiment the Si/Al ratio can range from 1.0 to 50. In an alternate embodiment the Si/Al ratio can range from 1.0 to 25.

Optional support materials may include silica, alumina, aluminosilica, titania, zirconia and combinations thereof, for example. An optional support material can be a larger crystal size faujasite, such as a conventional sized zeolite, that can support a nanosize zeolite.

The catalyst generally includes from 1 wt. % to 99 wt. %, or from 3 wt. % to 90 wt. % or from 4 wt. % to 80 wt. % nanosize zeolite in the final catalyst, for example. In an embodiment the nanosize zeolite ranges from 5 wt. % to 50 wt. %, optionally from 5 wt. % to 30 wt. %. In one or more embodiments, the catalyst includes from 5 wt. % to 20 wt. %, or from 5 wt. % to 15 wt. % or from 7 wt. % to 12 wt. % support material in the final catalyst, for example.

In one or more embodiments, the nanosize zeolite may have an increased ratio of surface area to volume compared to zeolitic materials that are not nanosize, for example. For example the nanosize zeolite may have at least 50% higher ratio of surface area to volume compared to zeolitic materials that are not nanosize, optionally at least 100% higher ratio, optionally at least two times higher ratio, optionally at least five times higher ratio, optionally at least ten times higher ratio.

The nanosize zeolite may be supported, or added, by any method(s) known to one skilled in the art. In an embodiment, these methods may include incipient wetness impregnation. In an alternative embodiment, the nanosize zeolite can be admixed with a support material. In a further embodiment, the nanosize zeolite may be supported in-situ with the support material or extruded. In an additional embodiment, the nanosize zeolite may be supported by spray-coating it onto a support material. It is further contemplated that such support processes may include layering the nanosize zeolite onto the support material, such as the support materials described below or optionally polymer spheres, such as polystyrene spheres, for example. It is even further contemplated that such support processes may include the utilization of zeolitic membranes, for example.

In one specific embodiment, the nanosize zeolite is supported by a support material and the nanosize zeolite is added to the support material via incipient wetness impregnation. In an embodiment, this process includes dispersing a nanosize zeolite in a diluent, such as non-limiting examples of methanol or toluene, to yield individually dispersed crystals, or individually dispersed nanoparticles. A support material may then be added to the solution and mixed until dry. In an embodiment, the dispersing of the nanoparticles of the nanosize zeolite in a solution is naturally dispersed or can be aided by agitation. Any suitable means of agitation can be used. In a specific embodiment, the agitation includes sonication.

In the incipient wetness impregnation method, the nanoparticles can have an affinity for one another and can form conglomerations inside the pores of the substrate. These conglomerations may become bound inside the support material, causing the nanosize zeolite to be supported by the support material. But conglomerations of the nanoparticles within the pores of the substrate are not necessary for the nanoparticles to be supported by the substrate.

In another embodiment, the nanoparticles may be added to the support aided by the use of carriers. In an embodiment, this process includes dispersing a nanosize zeolite in a diluent, such as methanol or toluene, to yield individually dispersed crystals, or individually dispersed nanoparticles. A support material may then be added to the solution and mixed. A carrier may be added to the solution at any point during the mixing. In an embodiment, the carrier is added to the diluent before the nanosize zeolite is added. In another embodiment, the carrier is added to the diluent after the nanosize zeolite is added and before the support material is added. In a further embodiment, the carrier is added after the nanosize zeolite and support material are added to the diluent. In an aspect, the zeolitic material, the catalytically active promoter, the support material or combinations thereof may optionally be contacted with a carrier prior to contact of the zeolitic material with the catalytically active promoter. This can be done by having an ion exchange, or other process of addition, performed after a supporting step. The carrier may be adapted to aid in the incorporation of the catalytically active promoter into the zeolitic material, for example. In one or more embodiments, the carrier is a nano-sized carrier, or nanocarrier (with the nano-sized carrier defined as for nanosize zeolites, as described above). In an embodiment, the carrier may include aluminum. In a more specific embodiment, the aluminum-containing carrier includes boehmite alumina. In an embodiment, the nanocarrier comprises material that can attract nanoparticles with columbic interaction.

In one embodiment, the nanosize zeolite is formed by utilizing a carrier to transport the nanosize zeolite into pores of the support material. In an embodiment, the carrier includes boehmite alumina. The carrier may be then be added to a solution containing toluene or methanol. Boehmite alumina is a nano-sized crystallite having particle sizes from about 10 to 15 nm. These nanoparticles have a high surface charge that can adhere small particles, such as nano-zeolites, which can be beneficial in transporting the zeolites into the pores of the silica support material. The formed zeolite may then be dried and subjected to thermal treatment. During thermal treatment, the silica and alumina can bond and hold the zeolite in a cage-like assembly for catalytic activity. In a further embodiment, the carrier may be mixed with a solvent prior to contact with the nanosize zeolite.

In an embodiment, the nanosize zeolite is supported by physical addition of the nanosize zeolite with the zeolitic support. In another embodiment, the nanosize zeolite is supported by forming an extrudable material utilizing a support material in combination with the nanosize zeolite to form extrudates and/or tablets.

The nanosize zeolite may be chemically modified so that it will graft onto a support. In an embodiment, the nanosize zeolite is supported by surface modification of the nanosize zeolite followed by grafting the modified nanosize zeolite onto a support. In an embodiment, the support is selected from the group of silica, alumina, a monolith structure and combinations thereof. In another embodiment, the nanosize zeolite is supported by a process including: surface modifying the nanosize zeolites using a grafting molecule such as a silane (silica having functional groups) to yield a surface modified nanosize zeolite, wherein the surface modified nanosize zeolite has terminal reactive functional groups which can help to graft the nanosize zeolite onto a support.

In an embodiment, the nanosize zeolite is deposited on a support by any suitable means, such as by non-limiting example one selected from the group of dip-coating, spray-coating, and wash-coating and any combinations thereof. The nanosize zeolite may be wash-coated on a monolith or an inert structured support for example.

The nanosize zeolite may be supported in situ with the support material. In an embodiment, the nanosize zeolite particles are created in situ with the support material. In another embodiment, the nanosize zeolite particles are simultaneously created and supported in situ with the support material.

The catalysts described herein may increase the effective diffusivity of the reactants, thereby increasing reactant conversion to desired products. Furthermore, the catalysts may result in processes exhibiting improved product selectivity over processes utilizing conventional zeolitic materials. In addition, activity of such processes may be increased due to an increase of accessibility of active sites, which thereby increases the effective number of active sites per weight of catalyst over larger non-nanosize zeolites.

Optionally, a catalytically active element, such as a catalytically active metal, may be incorporated into the nanosize zeolite by, for example, ion-exchange or impregnation of the zeolitic material, or by incorporating the active element in the synthesis materials from which the zeolitic material is prepared. As described herein, the term "incorporated into the zeolitic material" refers to incorporation into the framework of the zeolitic material, incorporation into channels of the zeolitic material (i.e., occluded) or combinations thereof.

The catalytically active element can be in a metallic form, combined with oxygen (e.g., metal oxide) or include derivatives of the compounds described below, for example. Suitable catalytically active metals depend upon the particular process in which the catalyst is intended to be used and generally include, but are not limited to, alkali metals (e.g., Li, Na, K, Rb, Cs, Fr), rare earth "lanthanide" metals (e.g., La, Ce, Pr), Group IVB metals (e.g., Ti, Zr, Hf), Group VB metals (e.g., V, Nb, Ta), Group VIB metals (e.g., Cr, Mo, W), Group IB metals (e.g., Cu, Ag, Au), Group VIIIB metals (e.g., Pd, Pt, Ir, Co, Ni, Rh, Os, Fe, Ru), Group IIIA metals (e.g., Ga), Group IVA metals (e.g., Ge) and combinations thereof, for example. Alternatively (or in combination with the previously discussed metals), the catalytically active element may include a Group IIIA compound (e.g., B), a Group VA compound (e.g., P) or combinations thereof, for example. In one or more embodiments, the catalytically active element is selected from Cs, Na, B, Ga and combinations thereof.

In one or more embodiments, the nanosize zeolite may include less than 15 wt. % sodium of the total weight of active catalyst, optionally less than 10 wt. % sodium, optionally less than 7 wt. % sodium. In one or more embodiments, the nanosize zeolite may include less than 25 wt. % aluminum of the total weight of active catalyst, optionally less than 20 wt. % aluminum, optionally less than 14 wt. % aluminum. In one or more embodiments, the nanosize zeolite may include at least 10 wt. % cesium of the total weight of active catalyst, optionally at least 20 wt. % cesium, optionally at least 25 wt. % cesium. In one or more embodiments, the nanosize zeolite may include less than 30 wt. % silicon of the total weight of active catalyst, optionally less than 25 wt. % silicon, optionally less than 18 wt. % silicon. In one or more embodiments, the nanosize zeolite may include less than 10 wt. % boron of the total weight of active catalyst, optionally less than 5 wt. % boron, optionally less than 3 wt. % boron. The balance of the nanosize zeolite will generally be formed of oxygen. If other elements are included in the material, then these amounts may be altered.

Increased side chain alkylation selectivity towards desired products may be achieved by treating the catalyst with chemical compounds to inhibit select basic sites. Such improvement may be accomplished by the addition of a second element. The second element can be one of those mentioned above. For example, in one or more embodiments, the second element may include boron.

The processes described herein may exhibit a toluene conversion of at least 0.01 mol. %, or from 0.05 mol. % to 80 mol. %, or from 2 mol. % to 25 mol. % or from 5 mol. % to 25 mol. % for example.

The process may exhibit a selectivity to styrene of at least 1 mol. %, or from 1 mol. % to 99 mol. %, or at least 30 mol. % or from 65 mol % to 99 mol %, for example.

The process may exhibit a selectivity to ethylbenzene of at least 5 mol. %, or from 5 mol. % to 99 mol. %, or at least 10 mol. % or from 8 mol % to 99 mol %, for example.

EXAMPLES

Example 1

A supported nanosize zeolite material was prepared according to the incipient wetness impregnation method. In this method, 18 mg of nanozeolite (Cs/Y) having a size of about 60 nm were dispersed in toluene and then loaded on to 570 mg of silica support.

Figure 3:
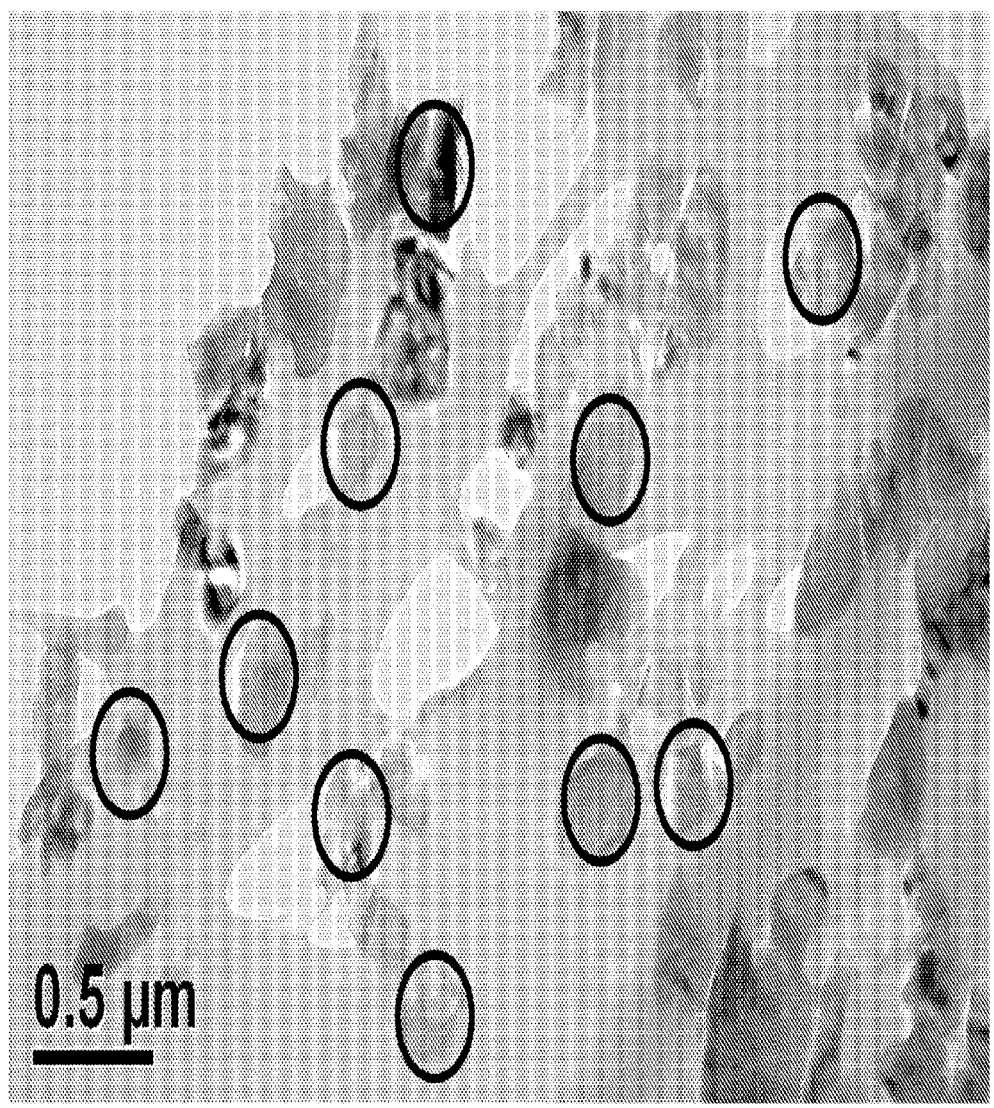
FIG. 3 is a Transmission Electron Microscopy (TEM) image of an embodiment of the present invention that shows nanozeolites incorporated in the pores of a silica substrate.

The Transmission Electron Microscopy (TEM) image in FIG. 3 shows that nanozeolites (Cs/Y), indicated by circles, are incorporated in the pores of the silica substrate and that they are well distributed.

Example 2

A supported nanosize zeolite material was prepared by utilizing nanocarriers. In this method, 2.18 g of nanozeolite (Cs/Y) having an average size as determined by TEM of about 60 nm were dispersed in 250 ml of toluene using sonication cycles creating a dispersion solution. Each sonication cycle was comprised of a five minute period at 450 watts and 21 amplitude level, followed by five minutes of inactivity to allow the solution to cool. This cycle was repeated three times, for a total of three cycles.

0.2 g of Catapal A alumina was added to the dispersion solution. Catapal A is a boehmite alumina, which is a nano-sized crystallite having sizes of about 10 to 15 nm. This boehmite alumina has a high surface charge that can adhere the small particles of the nanozeolites. The Catapal A is used as the nanocarrier. The mixture was then sonicated for five cycles.

10.09 g of silica having an average pore diameter of about 379 nm size as determined by TEM, a pore volume of 0.78 cc/g, and bulk density of 0.49 cc/g was then placed in an ion exchange column having an interior diameter of 1 inch. The dispersion solution was then added to the 10.09 g of silica in the ion exchange column. After the silica substrate was completely wet, the excess liquid was drained out and then left in a hood to air dry, followed by drying in a vented drying oven at 70° C. for 1 hr. This was repeated 19 times until the dispersion liquid was consumed.

The samples for TEM analysis were prepared by embedding the sample in an epoxy resin and curing the resin. The cured resin is then microtomed to ultra thin sections containing the cross-sections of the nanozeolites incorporated within the silica. The microtomed sections are placed on to the carbon film coated copper grid for TEM investigation.

Figure 4:
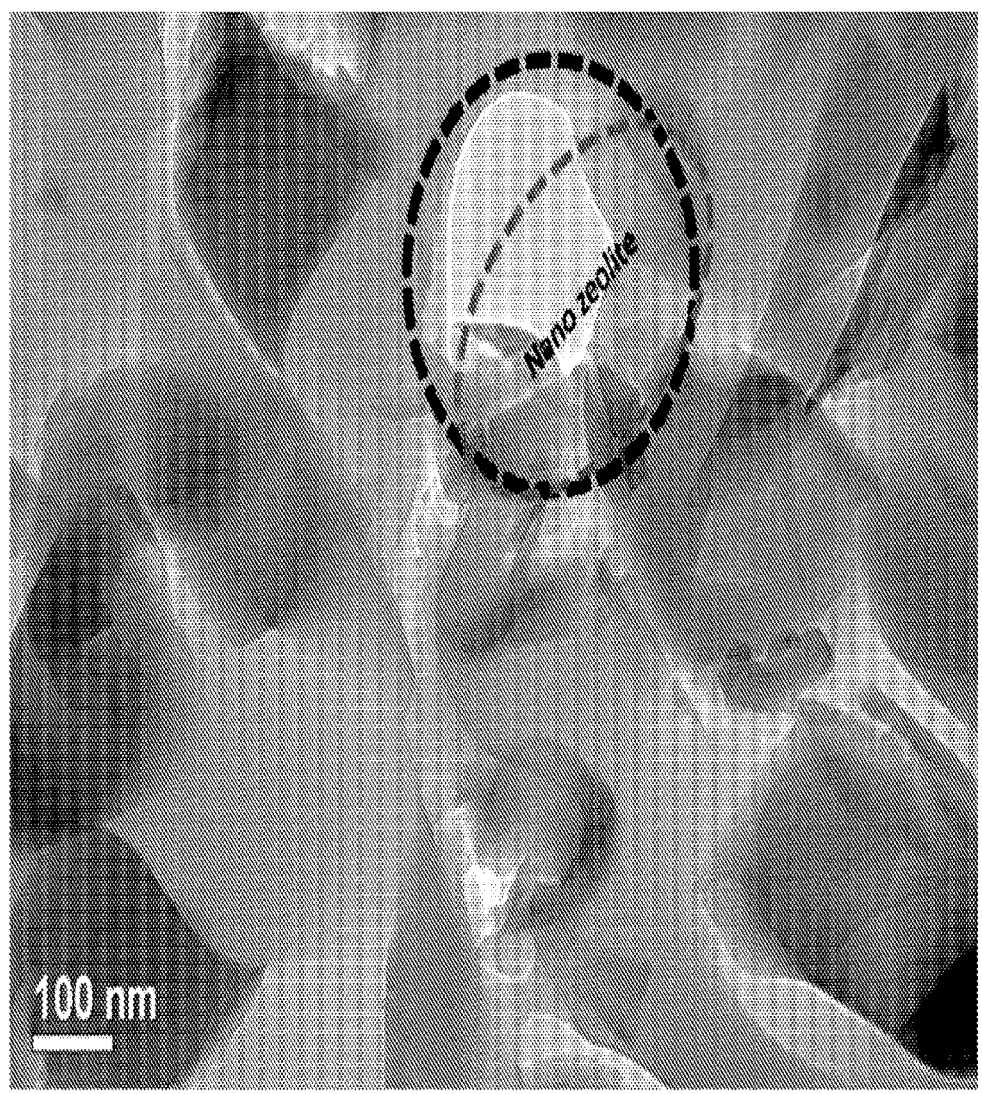
FIG. 4 is a TEM image of an embodiment of the present invention that shows distribution of nanocarriers and nanozeolites incorporated in the pores of a silica substrate.

The image in FIG. 4 shows distribution of nanocarriers (Catapal-A-alumina) as indicated by the larger dashed circle, along with the nanozeolites (Cs/Y), as indicated by the smaller dashed oval, incorporated in the pores of the silica substrate.

Figure 5:
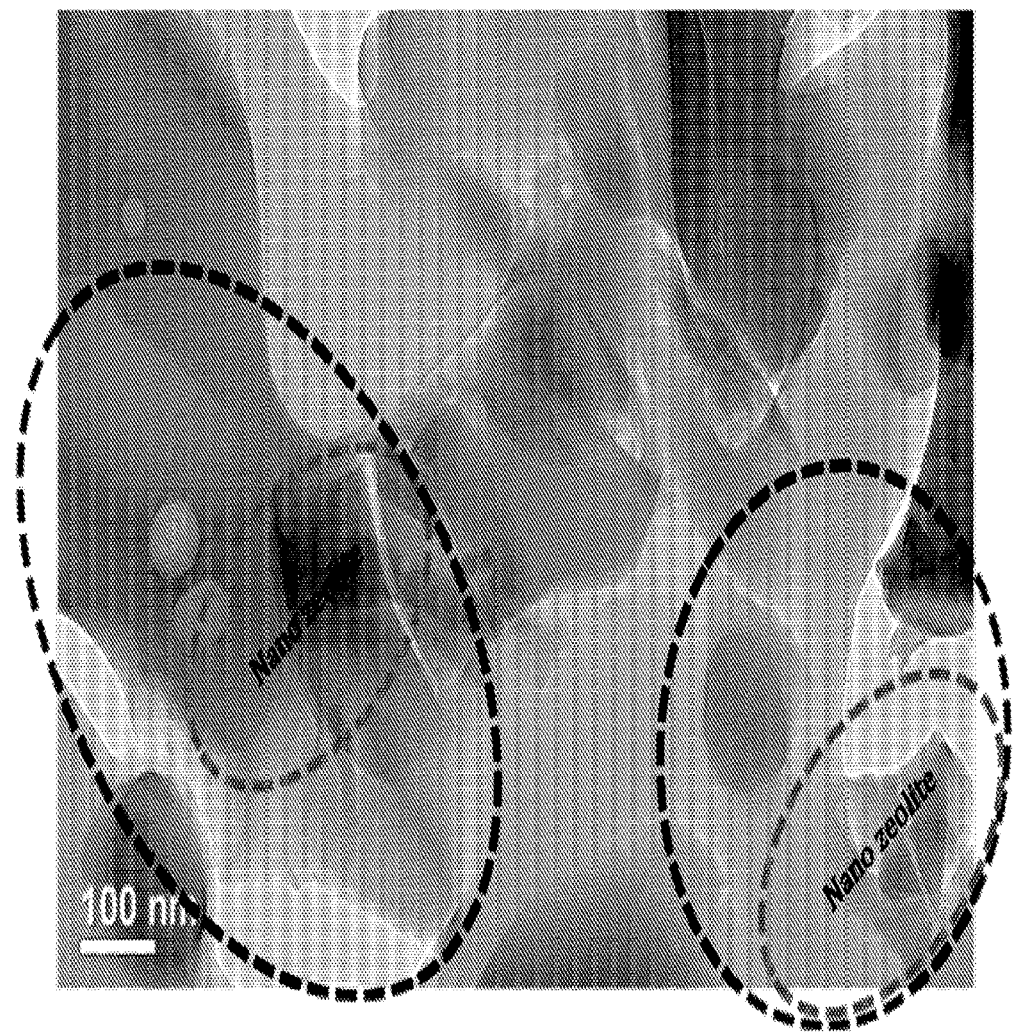
FIG. 5 is a TEM image of an embodiment of the present invention that shows a nanozeolite incorporated silica sample after use as a catalyst in an alkylation reaction of toluene and methanol.

The catalyst containing nanozeolites incorporated along with nanocarrier Catapal-A-alumina on the silica substrate was then subjected to a bench scale reaction of toluene and methanol (1:1 molar ratio; 22 cc/hr) in a 0.75-inch diameter stainless steel tube for a period of 5 hrs under alkylation conditions of 425° C., 3.5 psig, and a contact time of from 2 to 3 seconds. After the reaction the catalyst was analyzed by TEM to identify the presence of nanozeolites. FIG. 5 is a TEM analysis of the nanozeolite incorporated silica sample after the ATM reaction, and shows that nanozeolites have adhered to the walls of the silica support and did not get washed out under the reaction conditions. The nanocarriers (Catapal-A-alumina) as indicated by the larger dashed circles, along with the nanozeolites (Cs/Y), as indicated by the smaller dashed ovals, were still found incorporated in the pores of the silica substrate.

As used herein, the term "activity" refers to the weight of product produced per weight of the catalyst used in a process at a standard set of conditions per unit time.

The term "conversion" refers to the percentage of reactant (e.g. toluene) that undergoes a chemical reaction.

$X_{Tol}$=conversion of toluene (mol %)=(Tol$_{in}$−Tol$_{out}$)/Tol$_{in}$ $X_{MeOH}$=conversion of methanol to styrene+ethylbenzene (mol %)

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

The term "monolith" as used herein refers to a honey-combed substrate, such as a ceramic or metal honeycombed substrate, that can contain a catalyst element.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "selectivity" refers to the relative activity of a catalyst in reference to a particular compound in a mixture. Selectivity is quantified as the proportion of a particular product relative to all other products.

$S_{Sty}$=selectivity of toluene to styrene (mol %)=Sty$_{out}$/Tol$_{converted}$ $S_{Bz}$=selectivity of toluene to benzene (mol %)=Benzene$_{out}$/Tol$_{converted}$ $S_{EB}$=selectivity of toluene to ethylbenzene (mol %)=EB$_{out}$/Tol$_{converted}$ $S_{Xyl}$=selectivity of toluene to xylenes (mol %)=Xylenes$_{out}$/Tol$_{converted}$ $S_{Sty+EB}$(MeOH)=selectivity of methanol to styrene+ethylbenzene (mol %)=(Sty$_{out}$+EB$_{out}$)/MeOH$_{converted}$ The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

While the foregoing is directed to embodiments of the present invention, other and further embodiments of the invention may be devised without departing from the basic scope thereof and the scope thereof is determined by the claims that follow.

What is claimed is:

1. A styrene production process comprising:
    providing a $C_1$ source, wherein the $C_1$ source is selected from methanol, formaldehyde, formalin, trioxane, methylformcel, paraformaldehyde and methylal and combinations thereof;
    contacting the $C_1$ source with toluene in the presence of a catalyst disposed within a reactor to form a product stream comprising styrene, wherein the catalyst comprises nanosize zeolite particles, wherein the nanosize zeolite particles comprise a Y-type zeolite, and wherein the catalyst is produced by:
    incorporating one or more catalytically active promoters into the nanosize zeolite particles, wherein the one or more catalytically active promoters are selected from the group consisting of Cs, Ga, B, Na, and combinations thereof;
    contacting and dispersing the nanosize zeolite particles with a solution to create a dispersion solution comprising dispersed nanosize zeolite particles;
    adding a nanocarrier to the dispersion solution prior to contacting the dispersion solution with a support material, wherein the nanocarrier comprises a silica oxide material or an aluminum-containing material;
    contacting the support material with the dispersion solution to create a wetted support and to thereby incorporate the nanosize zeolite particles into the support material; and
    drying the wetted support to obtain a catalyst; and
    recovering the product stream from the reactor.

2. The process of claim 1, further comprising
    contacting the nanosize zeolite particles with a silane resulting in a modified nanosize zeolite;
    grafting the modified nanosize zeolite onto a support; and
    calcining the modified nanosize zeolite grafted onto the support, resulting in a catalyst comprising nanosize zeolite particles.

3. The process of claim 1, wherein the catalyst is produced by physically combining nanosize zeolite particles with a support to form extrudates.

4. The process of claim 1, wherein the catalyst is produced by simultaneously creating and supporting nanosize zeolite particles in situ with the support material.

5. The process of claim 1, further comprising converting a $C_1$ source to form an intermediate product selected from formaldehyde, hydrogen, water, methanol and combinations thereof.

6. The process of claim 1, wherein the $C_1$ source comprises a mixture of methanol and formaldehyde.

7. The process of claim 1, wherein the nanosize zeolite particles have a particle size of less than about 1000 nm.

8. The process of claim 1, wherein the nanocarrier comprises a silica oxide material or an aluminum containing material.

9. The process of claim 1, wherein the nanocarrier comprises boehmite alumina.

* * * * *